United States Patent
Zielinski et al.

(10) Patent No.: US 8,140,155 B2
(45) Date of Patent: Mar. 20, 2012

(54) INTERMITTENT PACING THERAPY DELIVERY STATISTICS

(75) Inventors: John R. Zielinski, Eagan, MN (US); Shantha Arcot-Krishnamurthy, Vadnais Heights, MN (US); Joseph M. Pastore, Mentor, OH (US); Jeffrey E. Stahmann, Ramsey, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 345 days.

(21) Appl. No.: 12/401,194

(22) Filed: Mar. 10, 2009

(65) Prior Publication Data

US 2009/0234416 A1  Sep. 17, 2009

Related U.S. Application Data

(60) Provisional application No. 61/035,715, filed on Mar. 11, 2008.

(51) Int. Cl.
*A61N 1/362* (2006.01)

(52) U.S. Cl. .......................................................... 607/9

(58) Field of Classification Search .................. None
See application file for complete search history.

(56) References Cited

U.S. PATENT DOCUMENTS

| | | | |
|---|---|---|---|
| 3,650,277 A | 3/1972 | Sjostrand et al. |
| 4,587,975 A | 5/1986 | Salo et al. |
| 4,730,619 A | 3/1988 | Koning et al. |
| 4,791,931 A | 12/1988 | Slate |
| 4,834,710 A | 5/1989 | Fleck |
| 4,919,133 A | 4/1990 | Chiang |
| 5,007,427 A | 4/1991 | Sukuki et al. |
| 5,024,222 A | 6/1991 | Thacker |
| 5,058,584 A | 10/1991 | Bourgeois |
| 5,072,458 A | 12/1991 | Suzuki |
| 5,111,818 A | 5/1992 | Suzuki et al. |
| 5,184,615 A | 2/1993 | Nappholz et al. |
| 5,199,428 A | 4/1993 | Obel et al. |
| 5,282,840 A | 2/1994 | Hudrlik |

(Continued)

FOREIGN PATENT DOCUMENTS

EP  0547734 A2  6/1993

(Continued)

OTHER PUBLICATIONS

"U.S. Appl. No. 11/030,575, Non-Final Office Action mailed Jul. 26, 2006", 10 pgs.

(Continued)

*Primary Examiner* — Carl H Layno
*Assistant Examiner* — Paula J Stice
(74) *Attorney, Agent, or Firm* — Schwegman, Lundberg & Woessner, P.A.

(57) ABSTRACT

This document discusses, among other things, an apparatus comprising an implantable cardiac depolarization sensing circuit, an electrical stimulation circuit, and a pacing mode controller. The pacing mode controller is configured to deliver pacing therapy according to a first pacing mode that is a normal operating mode, and to deliver pacing therapy according to second and third pacing modes. The second and third pacing modes increase mechanical stress on at least a particular portion of the ventricle as compared to the pacing therapy delivered during the first pacing mode. The pacing mode controller alternates between the second and third pacing modes when switched from the normal operating mode to a stress augmentation mode and stores a statistic related to the stress augmentation mode in a stress augmentation cycle memory area.

21 Claims, 4 Drawing Sheets

U.S. PATENT DOCUMENTS

| | | | |
|---|---|---|---|
| 5,376,106 A | 12/1994 | Stahmann et al. |
| 5,484,419 A | 1/1996 | Fleck |
| 5,588,432 A | 12/1996 | Crowley |
| 5,755,671 A | 5/1998 | Albrecht et al. |
| 5,824,021 A | 10/1998 | Rise |
| 6,021,350 A | 2/2000 | Mathson |
| 6,058,331 A | 5/2000 | King |
| 6,104,956 A | 8/2000 | Naritoku et al. |
| 6,108,577 A | 8/2000 | Benser |
| 6,115,628 A | 9/2000 | Stadler et al. |
| 6,233,486 B1 | 5/2001 | Ekwall et al. |
| 6,238,422 B1 | 5/2001 | Oort |
| 6,256,538 B1 | 7/2001 | Ekwall |
| 6,272,379 B1 | 8/2001 | Fischell et al. |
| 6,285,907 B1 | 9/2001 | Kramer et al. |
| 6,314,323 B1 | 11/2001 | Ekwall |
| 6,408,208 B1 | 6/2002 | Sun |
| 6,411,845 B1 | 6/2002 | Mower |
| 6,445,953 B1 | 9/2002 | Bulkes et al. |
| 6,477,402 B1 | 11/2002 | Lynch et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,763,267 B2 | 7/2004 | Ding |
| 6,838,471 B2 | 1/2005 | Tracey |
| 6,842,642 B2 | 1/2005 | Vanhout |
| 6,845,267 B2 | 1/2005 | Harrison et al. |
| 6,865,420 B1 | 3/2005 | Kroll |
| 6,892,095 B2 | 5/2005 | Salo |
| 6,907,285 B2 | 6/2005 | Denker et al. |
| 6,937,899 B2 | 8/2005 | Sheldon et al. |
| 6,950,701 B2 | 9/2005 | Begemann et al. |
| 6,965,797 B2 | 11/2005 | Pastore et al. |
| 6,973,349 B2 | 12/2005 | Salo |
| 7,010,345 B2 | 3/2006 | Hill et al. |
| 7,025,730 B2 | 4/2006 | Cho et al. |
| 7,062,314 B2 | 6/2006 | Zhu et al. |
| 7,062,325 B1 | 6/2006 | Krig et al. |
| 7,069,070 B2 | 6/2006 | Carlson et al. |
| 7,092,755 B2 | 8/2006 | Florio |
| 7,158,832 B2 | 1/2007 | Kieval et al. |
| 7,215,992 B2 | 5/2007 | Stahmann et al. |
| 7,277,761 B2 | 10/2007 | Shelchuk |
| 7,295,874 B2 | 11/2007 | Prinzen et al. |
| 7,333,854 B1 | 2/2008 | Brewer et al. |
| 7,366,568 B2 | 4/2008 | Pastore et al. |
| 7,437,191 B2 | 10/2008 | Pastore et al. |
| 2002/0026222 A1 | 2/2002 | Schauerte et al. |
| 2002/0042632 A1 | 4/2002 | Iaizzo et al. |
| 2002/0072776 A1 | 6/2002 | Osorio et al. |
| 2002/0072777 A1 | 6/2002 | Lu |
| 2002/0082660 A1 | 6/2002 | Stahmann et al. |
| 2002/0091415 A1 | 7/2002 | Lovett et al. |
| 2002/0123772 A1 | 9/2002 | Sun et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0060854 A1 | 3/2003 | Zhu |
| 2003/0105493 A1 | 6/2003 | Salo |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0158584 A1 | 8/2003 | Cates et al. |
| 2003/0199956 A1 | 10/2003 | Struble et al. |
| 2003/0204206 A1 | 10/2003 | Padua et al. |
| 2003/0204231 A1 | 10/2003 | Hine et al. |
| 2003/0229380 A1 | 12/2003 | Adams et al. |
| 2003/0233130 A1 | 12/2003 | Padmanabhan et al. |
| 2004/0015081 A1 | 1/2004 | Kramer et al. |
| 2004/0038947 A1 | 2/2004 | Wink et al. |
| 2004/0088015 A1 | 5/2004 | Casavant et al. |
| 2004/0088017 A1 | 5/2004 | Sharma et al. |
| 2004/0102815 A1 | 5/2004 | Balczewski et al. |
| 2004/0106960 A1 | 6/2004 | Siejko et al. |
| 2004/0106961 A1 | 6/2004 | Siejko et al. |
| 2004/0133247 A1 | 7/2004 | Stahmann et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0075673 A1 | 4/2005 | Warkentin et al. |
| 2005/0090719 A1 | 4/2005 | Scheiner et al. |
| 2005/0096705 A1 | 5/2005 | Pastore et al. |
| 2005/0096706 A1 | 5/2005 | Salo |
| 2005/0131467 A1 | 6/2005 | Boveja |
| 2005/0137631 A1 | 6/2005 | Yu et al. |
| 2005/0149126 A1 | 7/2005 | Libbus |
| 2005/0149127 A1 | 7/2005 | Libbus |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0195038 A1 | 8/2006 | Carlson et al. |
| 2006/0241704 A1 | 10/2006 | Shuros et al. |
| 2006/0247700 A1 | 11/2006 | Jackson |
| 2006/0253156 A1 | 11/2006 | Pastore et al. |
| 2006/0259087 A1 | 11/2006 | Baynham et al. |
| 2006/0259088 A1 | 11/2006 | Pastore et al. |
| 2006/0287684 A1 | 12/2006 | Baynham et al. |
| 2007/0021789 A1 | 1/2007 | Pastore et al. |
| 2007/0021790 A1 | 1/2007 | Kieval et al. |
| 2007/0021798 A1 | 1/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0043393 A1 | 2/2007 | Brockway et al. |
| 2007/0060972 A1 | 3/2007 | Kieval et al. |
| 2007/0142864 A1 | 6/2007 | Libbus et al. |
| 2007/0142871 A1 | 6/2007 | Libbus et al. |
| 2007/0150005 A1 | 6/2007 | Sih et al. |
| 2007/0167984 A1 | 7/2007 | Kieval et al. |
| 2007/0239218 A1 | 10/2007 | Carlson et al. |
| 2007/0299356 A1 | 12/2007 | Wariar et al. |
| 2008/0015659 A1 | 1/2008 | Zhang et al. |
| 2008/0021507 A1 | 1/2008 | Libbus et al. |
| 2008/0027495 A1 | 1/2008 | Prinzen et al. |
| 2008/0140141 A1 | 6/2008 | Ben-David et al. |
| 2008/0167694 A1 | 7/2008 | Bolea et al. |
| 2008/0215105 A1 | 9/2008 | Pastore et al. |
| 2009/0192560 A1 | 7/2009 | Arcot-Krishnamurthy et al. |

FOREIGN PATENT DOCUMENTS

| | | |
|---|---|---|
| EP | 1437159 A1 | 7/2004 |
| WO | WO-9518649 A1 | 7/1995 |
| WO | WO-0115609 A1 | 3/2001 |
| WO | WO-0124876 A1 | 4/2001 |
| WO | WO-0128625 | 4/2001 |
| WO | WO-0176689 A2 | 10/2001 |
| WO | WO-03082080 A2 | 10/2003 |
| WO | WO-2004058326 A2 | 7/2004 |
| WO | WO-2005042091 A1 | 5/2005 |
| WO | WO-2006074189 A1 | 7/2006 |
| WO | WO-2006079010 A1 | 7/2006 |
| WO | WO-2006115693 A2 | 11/2006 |
| WO | WO-2006115693 A3 | 11/2006 |
| WO | WO-2006121842 A2 | 11/2006 |
| WO | WO-2006124636 A2 | 11/2006 |
| WO | WO-2006124729 A2 | 11/2006 |
| WO | WO-2007078410 A1 | 7/2007 |
| WO | WO-2007133962 A2 | 11/2007 |
| WO | WO-2008063396 A1 | 5/2008 |

OTHER PUBLICATIONS

"U.S. Appl. No. 11/030,575, Notice of Allowance mailed Jan. 17, 2007", 7 pgs.

"U.S. Appl. No. 11/030,575, Notice of Allowance mailed Jun. 7, 2007", 7 pgs.

"U.S. Appl. No. 11/030,575, Response filed Oct. 26, 2006 to Non-Final Office Action mailed Jul. 26, 2006", 8 pgs.

"U.S. Appl. No. 11/129,050, Advisory Action mailed Jul. 14, 2009", 3 pgs.
"U.S. Appl. No. 11/129,050, Advisory Action mailed Jul. 28, 2008", 3 pgs.
"U.S. Appl. No. 11/129,050, Examiner Interview Summary mailed Feb. 11, 2009", 2 pgs.
"U.S. Appl. No. 11/129,050, Final Office Action mailed Apr. 21, 2009", 10 pgs.
"U.S. Appl. No. 11/129,050, Final Office Action mailed May 12, 2008", 8 pgs.
"U.S. Appl. No. 11/129,050, Non-Final Office Action mailed Nov. 6, 2008", 7 pgs.
"U.S. Appl. No. 11/129,050, Non-Final Office Action mailed Nov. 26, 2007", 7 pgs.
"U.S. Appl. No. 11/129,050, Notice of Allowance mailed Apr. 1, 2010", 6 pgs.
"U.S. Appl. No. 11/129,050, Notice of Allowance mailed Jul. 16, 2010", 4 pgs.
"U.S. Appl. No. 11/129,050, Notice of Allowance mailed Aug. 24, 2009", 7 pgs.
"U.S. Appl. No. 11/129,050, Notice of Allowance mailed Nov. 1, 2010", 6 pgs.
"U.S. Appl. No. 11/129,050, Notice of Allowance mailed Dec. 2, 2009", 4 pgs.
"U.S. Appl. No. 11/129,050, Response filed Feb. 23, 2009 to Non-Final Office Action mailed Nov. 6, 2008", 13 pgs.
"U.S. Appl. No. 11/129,050, Response filed Feb. 26, 2008 to Non-Final Office Action mailed Nov. 26, 2007", 14 pgs.
"U.S. Appl. No. 11/129,050, Response filed Jun. 22, 2009 to Final Office Action mailed Apr. 21, 2009", 9 pgs.
"U.S. Appl. No. 11/129,050, Response filed Jul. 14, 2008 to Final Office Action mailed May 12, 2008", 13 pgs.
"U.S. Appl. No. 11/129,050, Response filed Sep. 28, 2007 to Restriction Requirement mailed Aug. 1, 2007", 11 pgs.
"U.S. Appl. No. 11/129,050, Restriction Requirement mailed Aug. 1, 2007", 6 pgs.
"U.S. Appl. No. 11/129,050, Supplemental Amendment and Response filed Sep. 12, 2008 to Final Office Action mailed May 12, 2008", 12 pgs.
"U.S. Appl. No. 11/129,058, Advisory Action mailed Oct. 17, 2007", 3 pgs.
"U.S. Appl. No. 11/129,058, Appeal Brief filed Jan. 8, 2008", 23 pgs.
"U.S. Appl. No. 11/129,058, Examiner's Answer mailed Jun. 18, 2008", 14 pgs.
"U.S. Appl. No. 11/129,058, Final Office Action mailed Jul. 9, 2007", 12 pgs.
"U.S. Appl. No. 11/129,058, Non-Final Office Action mailed Jan. 29, 2007", 11 pgs.
"U.S. Appl. No. 11/129,058, Response filed Apr. 30, 2007 to Non-Final Office Action mailed Jan. 29, 2007", 16 pgs.
"U.S. Appl. No. 11/129,058, Response filed Oct. 9, 2007 to Final Office Action mailed Jul. 9, 2007", 14 pgs.
"U.S. Appl. No. 11/151,015, Non-Final Office Action mailed May 21, 2007", 10 pgs.
"U.S. Appl. No. 11/151,015, Notice of Allowance mailed Dec. 6, 2007", 6 pgs.
"U.S. Appl. No. 11/151,015, Response filed Aug. 21, 2007 to Non-Final Office Action mailed May 21, 2007", 9 pgs.
"U.S. Appl. No. 11/207,251, Final Office Action mailed Feb. 3, 2009", 9 pgs.
"U.S. Appl. No. 11/207,251, Non-Final Office Action mailed Jun. 27, 2008", 8 pgs.
"U.S. Appl. No. 11/207,251, Notice of Allowance mailed May 28, 2009", 4 pgs.
"U.S. Appl. No. 11/207,251, Notice of Allowance mailed Sep. 28, 2009", 4 pgs.
"U.S. Appl. No. 11/207,251, Response filed Apr. 7, 2009 to Final Office Action mailed Feb. 3, 2009", 11 pgs.
"U.S. Appl. No. 11/207,251, Response filed Sep. 29, 2008 to Non-Final Office Action mailed Jun. 27, 2008", 14 pgs.
"U.S. Appl. No. 11/318,263, Advisory Action mailed Aug. 18, 2010", 3 pgs.
"U.S. Appl. No. 11/318,263, Final Office Action mailed Mar. 17, 2009", 11 pgs.
"U.S. Appl. No. 11/318,263, Final Office Action mailed Jun. 2, 2010", 10 pgs.
"U.S. Appl. No. 11/318,263, Non-Final Office Action mailed Nov. 27, 2009", 8 pgs.
"U.S. Appl. No. 11/318,263, Non-Final Office Action mailed Aug. 20, 2008", 9 pgs.
"U.S. Appl. No. 11/318,263, Notice of Allowance mailed Sep. 29, 2010", 6 pgs.
"U.S. Appl. No. 11/318,263, Response filed Feb. 26, 2010 to Non-Final Office Action mailed Nov. 27, 2009", 11 pgs.
"U.S. Appl. No. 11/318,263, Response filed May 18, 2009 to Final Office Action mailed Mar. 17, 2009", 12 pgs.
"U.S. Appl. No. 11/318,263, Response filed May 22, 2008 to Restriction Requirement mailed Apr. 23, 2008", 10 pgs.
"U.S. Appl. No. 11/318,263, Response filed Aug. 2, 2010 to Final Office Action mailed Jun. 3, 2010", 13 pgs.
"U.S. Appl. No. 11/318,263, Response filed Aug. 12, 2009 to Restriction Requirement mailed Jul. 14, 2009", 9 pgs.
"U.S. Appl. No. 11/318,263, Response filed Nov. 20, 2008 to Non-Final Office Action mailed Aug. 20, 2008", 12 pgs.
"U.S. Appl. No. 11/318,263, Restriction Requirement mailed Apr. 23, 2008", 7 pgs.
"U.S. Appl. No. 11/318,263, Restriction Requirement mailed Jul. 14, 2009", 5 pgs.
"International Application Serial No. PCT/US2006/000125, International Search Report and Written Opinion mailed May 11, 2006", 12 pgs.
"International Application Serial No. PCT/US2006/017384, International Search Report and Written Opinion mailed Jan. 23, 2007", 12 pgs.
"International Application Serial No. PCT/US2006/018642, International Search Report and Written Opinion mailed Oct. 24, 2006", 14 pgs.
"International Application Serial No. PCT/US2007/068217, International Search Report mailed Oct. 30, 2007", 5 pgs.
"International Application Serial No. PCT/US2007/068217, Written Opinion mailed Oct. 30, 2007", 8 pgs.
Andersen, H, et al., "Long-term follow-up of patients from a randomised trial of atrial versus ventricular pacing for sick-sinus syndrome", Lancet, 350(9086), (Oct. 25, 1997), 1210-6.
Benchimol, A, et al., "Cardiac hemodynamics during stimulation of the right atrium, right ventricle, and left ventricle in normal and abnormal hearts", Circulation, 33(6), (Jun. 1966), 933-44.
Grassi, Guido, et al., "Baroreflex and non-baroreflex modulation of vagal cardiac control after myocardial infarction", Am J Cardiol., 84(5), (Sep. 1, 1999), 525-529.
Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.
Kloner, R. A., et al., "Prospective temporal analysis of the onset of preinfarction angina versus outcome: an ancillary study in TIMI-9B", Circulation, 97(11), (1998), 1042-5.
Koning, M M, "Rapid ventricular pacing produces myocardial protection by nonischemic activation of KATP+ channels", Circulation, 93(1), (Jan. 1, 1996), 178-186.
Leclercq, C, et al., "Hemodynamic importance of preserving the normal sequence of ventricular activation in permanent cardiac pacing", Am Heart J., 129(6), (Jun. 1995), 1133-41.
Loukogeorgakis, S. P., et al., "Remote ischemic preconditioning provides early and late protection against endothelial ischemia-reperfusion injury in humans: role of the autonomic nervous system.", J Am Coll Cardiol., 46(3), (Aug. 2, 2005), 450-6.
Meier, B., et al., "Coronary Pacing During Percutaneous Transluminal Coronary Angioplasty", Circulation, 71(3), (Mar. 1985), 557-561.
Murry, C. E., et al., "Preconditioning with ischemia: a delay of lethal cell injury in ischemic myocardium", Circulation, 74(5), (1986), 1124-1136.
Ovize, M., et al., "Stretch preconditions canine myocardium.", Am J Physiol., 266(1 Pt 2), (Jan. 1994), H137-46.

Rosa, A., et al., "Ectopic Pacing at Physiological Rate Improves Postanoxic Recovery of the Developing Heart", Am. J. Physiol.—Heart Circ. Physiol., 284, (2003), H2384-H2392.

Rosenqvist, M, et al., "The effect of ventricular activation sequence on cardiac performance during pacing", Pacing and Electrophysiology, 19(9), (1996), 1279-1286.

Tsang, A., et al., "Postconditioning: a form of "modified reperfusion" protects the myocardium by activating the phosphatidylinositol 3-kinase-Akt pathway", Circ Res., 95(3), Epub 2004 Jul. 8., (Aug. 6, 2004), 230-2.

Vanagt, W. Y. R., et al., "Ventricular Pacing for Improving Myocardial Tolerance to Ischemic", Progress Report on Project Guidant-CARIM, (Oct. 2003), 1-25.

Vegh, A, et al., "Transient ischaemia induced by rapid cardiac pacing results in myocardial preconditioning", Cardiovascular Research, 25(12), (Dec. 1991), 1051-3.

Wu, Zhong-Kai, et al., "Ischemic preconditioning suppresses ventricular tachyarrhythmias after myocardial revascularization", Circulation, 106(24), (Dec. 10, 2002), 3091-3096.

Yang, S. M., et al., "Multiple, brief coronary occlusions during early reperfusion protect rabbit hearts by targeting cell signaling pathways", Journal of the American College of Cardiology, 44(5), (Sep. 1, 2004), 1103-1110.

Zhao, et al., "Inhibition of myocardial injury by ischemic postconditioning during reperfusion: comparison with ischemic preconditioning", Am J Physiol Heart Circ Physiol, 285(2), (Aug. 2003), H579-H588.

INTERMITTENT PACING THERAPY DELIVERY STATISTICS

RELATED APPLICATIONS

This application claims the benefit under 35 U.S.C. 119(e) of U.S. Provisional Patent Application Ser. No. 61/035,715, filed on Mar. 11, 2008, which is incorporated herein by reference in it entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Sometimes patients who receive IMDs have experienced heart failure (HF) decompensation or other events associated with worsening HF. Worsening HF may cause deteriorating hemodynamic performance that could lead to the inability to carry out daily activities and even could lead to death of the patient. Symptoms associated with worsening HF may include progressive decline in ejection fraction called progressive ventricular dilatation. Electrical pacing therapy may prevent progressive ventricular dilatation.

Overview

This document relates generally to apparatuses, systems, and methods to provide electrical pacing therapy to a patient or subject. In example 1, an apparatus includes an implantable cardiac depolarization sensing circuit, an electrical stimulation circuit, and a pacing mode controller. The cardiac depolarization sensing circuit is configured to obtain a sensed depolarization signal from a ventricle and the electrical stimulation circuit is configured to provide pacing electrical stimulation energy to an implantable ventricular electrode. The pacing mode controller is configured to deliver pacing therapy according to a first pacing mode that is a normal operating mode, and to deliver pacing therapy according to a second pacing mode and a third pacing mode different from the second pacing mode. The second and third pacing modes increase mechanical stress on at least a particular portion of the ventricle as compared to the pacing therapy delivered during the first pacing mode. The pacing mode controller alternates between the second and third pacing modes when switched from the normal operating mode to a stress augmentation mode and stores information related to the stress augmentation mode in a stress augmentation cycle memory area.

In example 2, the information related to the stress augmentation mode of example 1 includes a statistic related to delivery of pacing in the stress augmentation mode. The statistic optionally includes at least one of: a total time pacing therapy is delivered according to the second and third pacing modes, a total number of electrical stimulation pulses delivered during the stress augmentation mode, a total number of sensed intrinsic ventricular depolarizations during the stress augmentation mode, a total number of sessions of pacing in the stress augmentation mode that were completed, or a total number of sessions of pacing in the stress augmentation mode that remain to be delivered.

In example 3, the information related to the stress augmentation mode of examples 1-2 includes a statistic related to inhibiting the stress augmentation mode. The statistic optionally includes at least one of: a total number of times that the stress augmentation mode was not initiated as scheduled due to high depolarization rate, a total number of times that the stress augmentation mode was aborted due to high depolarization rate, a total number of times that the stress augmentation mode was aborted due to device reasons, a total number of times that the stress augmentation mode was retried when the stress augmentation mode was not initiated as scheduled, or a total number of times that a stress augmentation mode session was skipped.

In example 4, the pacing mode controller of examples 1-3 is optionally configured to store a plurality of statistics related to the stress augmentation mode as a log in the stress augmentation cycle memory area. In example 5, the pacing mode controller of examples 1-4 is optionally configured to create, in the stress augmentation cycle memory area, a log entry for a stress augmentation mode session that optionally includes at least one of: a session start time, a start time of the second pacing mode, a start time of the third pacing mode, a pacing rate at which the second pacing mode was delivered, a NASPE/BPEG (North American Society of Pacing and Electrophysiology/British Pacing and Electrophysiology Group)-defining pacing mode of the second pacing mode, a pacing rate at which the third pacing mode was delivered, a NASPE/BPEG-defined pacing mode of the third pacing mode, a count of electrical stimulation pulses delivered during the second pacing mode, a count of V intrinsic depolarizations sensed during the third pacing mode, a status of the stress augmentation mode session, a number of retries attempted in the stress augmentation mode session, data related to a physiologic cardiovascular event of a subject recorded during the stress augmentation mode session, or a measurement obtained from the recorded data.

In example 6, the pacing mode controller of examples 1-5 is optionally configured to create, in the stress augmentation cycle memory area, a log entry for a stress augmentation mode session that includes a NASPE/BPEG-defined pacing mode used during the stress augmentation session together with a pacing rate at which the NASPE/BPEG-defined pacing mode was delivered.

In example 7, a method includes delivering pacing therapy using an implantable device according to a first pacing mode that is a normal operating mode, and delivering pacing therapy according to a second pacing mode and a third pacing mode different from the second pacing mode. The second pacing mode and the third pacing mode increase mechanical stress on at least a particular portion of the ventricle as compared to the pacing therapy delivered during the first pacing mode. The method also includes alternating between the second and third pacing modes when switched from the normal operating mode to a stress augmentation mode, and storing, in the implantable device, information related to the stress augmentation mode.

In example 8, the storing information related to the stress augmentation mode of example 7 includes storing a statistic related to delivery of pacing in the stress augmentation mode. The statistic optionally includes at least one of: a total time pacing therapy is delivered according to the second and third pacing modes, a total number of ventricular (V) pace stimulation pulses delivered during the stress augmentation mode, a total number of sensed intrinsic V depolarizations during the stress augmentation mode, a total number of sessions of pacing in the stress augmentation mode that were completed, or a total number of sessions of pacing in the stress augmentation mode that remains to be delivered.

In example 9, the storing information related to the stress augmentation mode of examples 7-8 optionally includes storing a statistic related to inhibiting the stress augmentation mode. The statistic optionally includes at least one of: a total number of times that the stress augmentation mode was not initiated as scheduled due to high depolarization rate, a total number of times that the stress augmentation mode was aborted due to high depolarization rate, a total number of times that the stress augmentation mode was aborted due to device reasons, a total number of times that the stress augmentation mode was retried when the stress augmentation mode was not initiated as scheduled, or a total number of times that a stress augmentation mode session was skipped.

In example 10, the storing information related to the stress augmentation mode of examples 7-9 optionally includes storing a plurality of statistics as a log in a memory of the implantable device. In example 11, the statistics of examples 7-10 optionally include at least one of: a session start time, a start time of the second pacing mode, a start time of the third pacing mode, a pacing rate at which the second pacing mode was delivered, a NASPE/BPEG-defined pacing mode of the second pacing mode, a pacing rate at which the third pacing mode was delivered, a NASPE/BPEG-defined pacing mode of the third pacing mode, a count of electrical stimulation pulses delivered during the second pacing mode, a count of V intrinsic depolarizations sensed during the third pacing mode, a status of the stress augmentation mode session, a number of retries attempted in the stress augmentation mode session, data related to a physiologic cardiovascular event of a subject recorded during the stress augmentation mode session, or a measurement obtained from the recorded data.

In example 12, the method of examples 7-11 optionally includes transferring a plurality of stored statistics from the implantable device to an external device, and presenting the stored statistics in a multilevel display. In example 13, the presenting the stored statistics in a multilevel display of examples 7-12 optionally includes presenting a first display level that includes a statistic related to delivery of pacing in the stress augmentation mode, and presenting a second display level that includes a statistic related to inhibiting the stress augmentation mode.

In example 14, the presenting the stored statistics in a multilevel display of examples 7-13 optionally includes presenting a first display level that includes a statistic related to delivery of pacing in the stress augmentation mode, and presenting a second display level that includes at least one stress augmentation session log entry stored in the implantable device. In example 15, the presenting the stored statistics in a multilevel display of examples 7-14 optionally includes presenting a first display level that includes a statistic related to delivery of pacing in the stress augmentation mode, and presenting a second display level that includes data related to a physiologic cardiovascular event of a subject recorded by the implantable device during a stress augmentation mode session.

In example 16, a system includes an implantable device and an external device. The implantable device includes a cardiac depolarization sensing circuit configured to obtain a sensed depolarization signal from a ventricle, an electrical stimulation circuit, configured to provide pacing electrical stimulation energy to at least one implantable electrode in the ventricle, a first communication circuit, and a pacing mode controller communicatively coupled to the cardiac depolarization sensing circuit, the electrical stimulation circuit, and the communication circuit. The pacing mode controller is configured to deliver pacing therapy according to a first pacing mode that is a normal operating mode, and to deliver pacing therapy according to a second pacing mode and a third pacing mode different from the second pacing mode. The second and third pacing modes increase mechanical stress on at least a particular portion of the ventricle as compared to the pacing therapy delivered during the first pacing mode. The pacing mode controller alternates between the second and third pacing modes when switched from the normal operating mode to a stress augmentation mode and communicates a plurality of stored statistics related to the stress augmentation mode to a second device via the first communication circuit. The external device includes a display, a second communication circuit configured to communicate information with the implantable device, and a processor communicatively coupled to the display and the second communication circuit. The processor is configured to receive the statistics from the implantable device, and present the statistics in a multilevel display.

In example 17, the implantable device of example 16 is optionally configured to communicate, to the external device, a statistic related to delivery of pacing in the stress augmentation mode and at least one log entry for a stress augmentation mode session. The processor of the external device of example 16 is optionally configured to present a first display level that includes the statistic related to delivery of pacing in the stress augmentation mode, and present a second display level that includes the log entry for a stress augmentation mode session.

In example 18, the implantable device of examples 16 and 17 is optionally configured to communicate, to the external device, a statistic related to delivery of pacing in the stress augmentation mode and data related to a physiologic cardiovascular events of a subject recorded by the implantable device during a stress augmentation mode session, and the processor of the external device of examples 16 and 17 is optionally configured to present a first display level that includes the statistic related to delivery of pacing in the stress augmentation mode, and present a second display level that includes the recorded data related to a physiologic cardiovascular event of the subject.

In example 19, the implantable device of examples 16-18 is optionally configured to communicate, to the external device, a statistic related to delivery of pacing in the stress augmentation mode and a statistic related to inhibiting the stress augmentation mode, and the processor of the external device of examples 16-18 is optionally configured to present a first display level that includes the statistic related to delivery of pacing in the stress augmentation mode, and present a second display level that includes the statistic related to inhibiting the stress augmentation mode.

In example 20, the implantable device of examples 16-19 is optionally configured to communicate, to the external device, at least one log entry for stress augmentation mode session and to communicate data related to a physiologic cardiovascular events of a subject recorded by the implantable device during the stress augmentation mode session, and the processor of the external device of examples 16-19 is optionally configured to present a third display level that includes the log entry for the stress augmentation session, and present a fourth display level that includes the recorded data related to a physiologic cardiovascular event of the subject.

In example 21, the system of examples 16-20 optionally includes a third device configured to communicate with the implantable device and the external device, and wherein the implantable device communicates the statistics related to the stress augmentation mode to the external device via the third device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
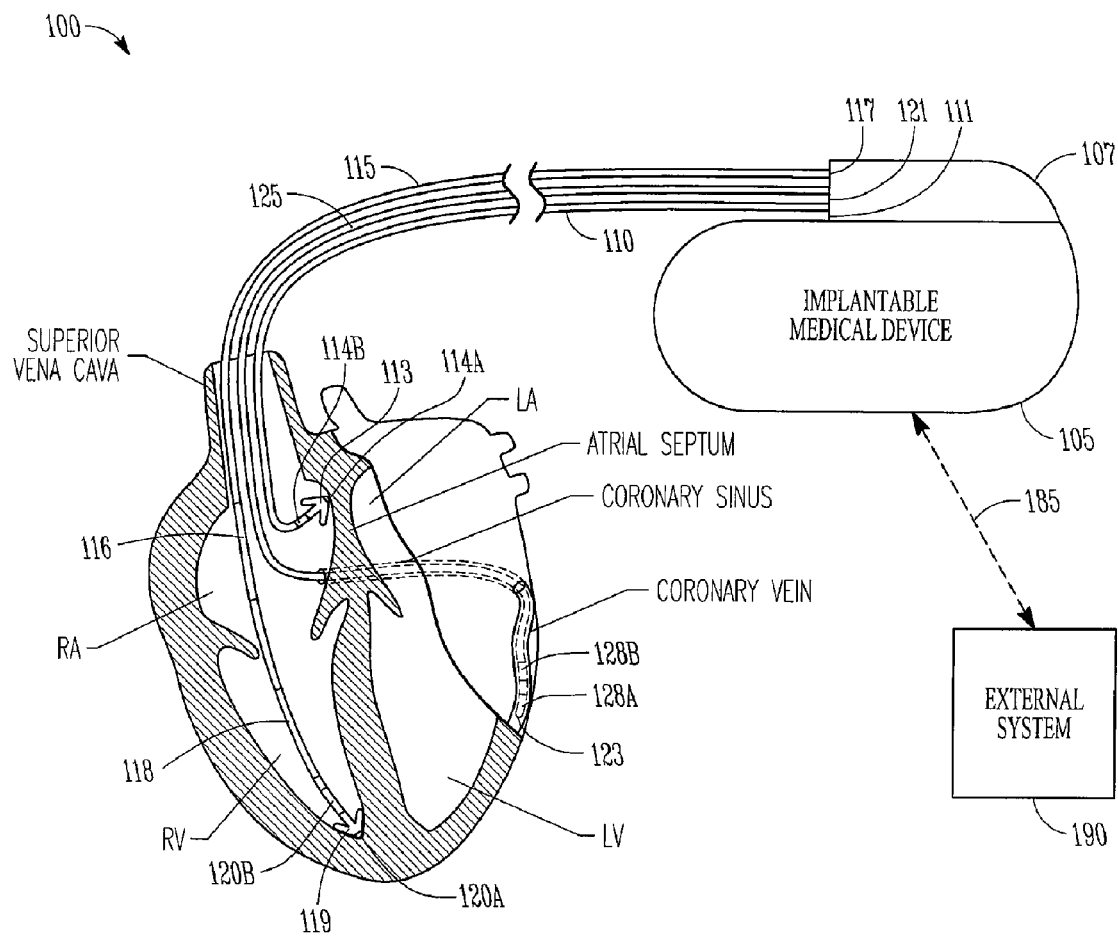
FIG. 1 is an illustration of portions of an example of a system that uses an IMD.

FIG. 1 is an illustration of portions of a system 100 that uses an MD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of MD 105 allow for sensing an RV electrogram signal representative of RV depolarizations and delivering RV pacing pulses. In some examples, the IMI includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

As discussed above, symptoms associated with worsening HF may include progressive ventricular dilatation, or a decline in ejection fraction. Occasionally causing dyssynchrony of ventricular contractions may prevent progressive ventricular dilatation. This dyssynchrony may be provided by an intermittent pacing therapy using an IMD. The intermittent pacing therapy is designed to increase ventricular dyssynchrony to cause stress in regional areas of the myocardial wall. The stress is caused in regions that are activated later than others. Providing this intermittent regional stress may halt progression of ventricular dilatation.

Figure 2:
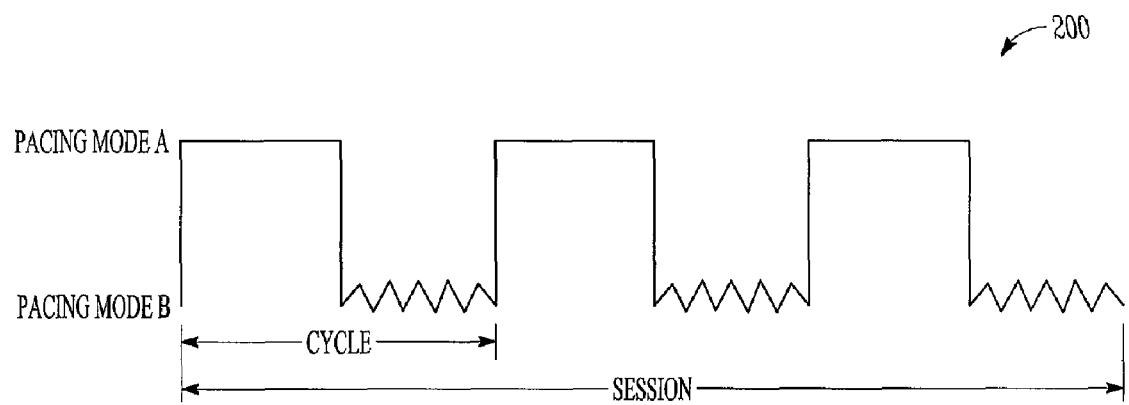
FIG. 2 is an illustration of a timing diagram of an example of intermittent pacing therapy provided by an IMD.

FIG. 2 is an illustration of a timing diagram 200 of an example of intermittent pacing therapy provided by an IMD. The timing diagram 200 shows an intermittent pacing therapy session. Prior to and after the intermittent pacing session, the IMD provides pacing therapy in a normal operating mode that allows for regular depolarizations to occur in the heart chamber (e.g., the NASPE/BPEG-defined DDD pacing mode). The intermittent pacing session includes three cycles of alternating Pacing Mode A with Pacing Mode B. The alternating of Pacing Mode A with Pacing Mode B increases mechanical stress on at least a particular portion of a ventricle as compared to the pacing therapy delivered during the normal operating mode. This intermittent pacing therapy can be referred to as a stress augmentation mode and is designed to provide control over the progression of ventricular dilatation.

Figure 3:
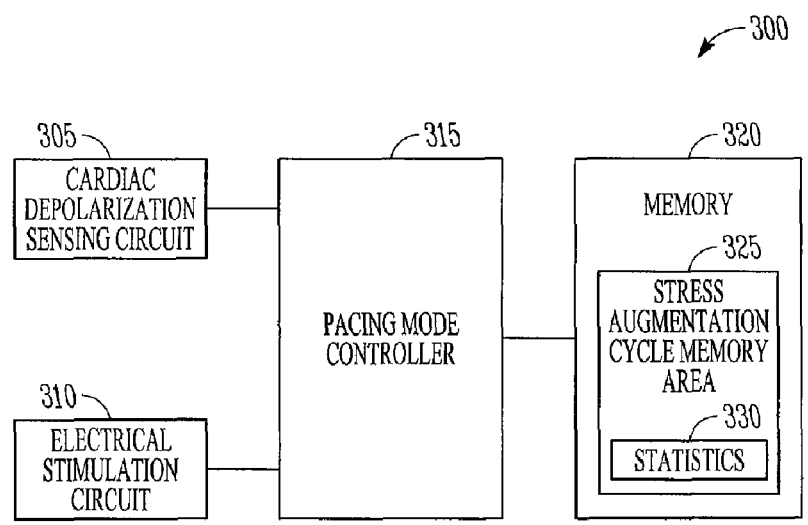
FIG. 3 is a block diagram of portions of an example of an IMD to provide intermittent pacing therapy in a stress augmentation mode.

FIG. 3 is a block diagram of portions of an IMD 300 to provide intermittent pacing therapy in a stress augmentation mode. The IMD 300 includes at least one implantable cardiac depolarization sensing circuit 305, an electrical stimulation circuit 310, and a pacing mode controller 315. The cardiac depolarization sensing circuit 305 obtains a sensed depolarization signal from a ventricle such as by using a sense amplifier circuit for example. The electrical stimulation circuit provides pacing electrical stimulation energy to at least one implantable ventricular electrode.

The pacing mode controller 315 may include a digital signal processor, application specific integrated circuit (ASIC), microprocessor, or other type of processor, interpreting or executing instructions in software or firmware. The pacing mode controller 315 may include any combination of hardware, firmware, or software. In some examples, the pacing mode controller 315 may include a state machine or sequencer that is implemented in hardware circuits.

The pacing mode controller 315 includes one or more circuits to perform the functions described herein. A circuit may include software, hardware, firmware or any combination thereof. For example, the circuit may include instructions in software executing on the pacing mode controller 315. Multiple functions may be performed by one or more circuits.

The pacing mode controller 315 is communicatively coupled to the cardiac depolarization sensing circuit 305 and the electrical stimulation circuit 310 (e.g., the pacing mode controller 315 is able to communicate signals with the cardiac depolarization sensing circuit 305 and the electrical stimulation circuit 310 even though there may be intervening circuitry coupled between them. The pacing mode controller 315 delivers pacing therapy (via the cardiac depolarization sensing circuit 305 and the electrical stimulation circuit 310) according to a first mode that is a normal operating mode. The pacing mode controller 315 also delivers intermittent pacing therapy in a stress augmentation mode.

When switched from the normal operating mode to the stress augmentation mode, the pacing mode controller 315 delivers pacing therapy according to a second pacing mode and a third pacing mode. The second pacing mode and the third pacing mode increase mechanical stress on at least a particular portion of the ventricle as compared to the pacing therapy delivered during the first pacing mode. The pacing mode controller 315 alternates pacing therapy between the second and third pacing modes (e.g., between Pacing mode A and Pacing B in FIG. 2) when switched from the normal operating mode to a stress augmentation mode.

In some examples, the cardiac depolarization sensing circuit 305 is configured to obtain a sensed depolarization signal from an atrium such as by placement of an implantable electrode in or near the atrium, and the electrical stimulation circuit is configured to provide pacing electrical stimulation energy to the atrial electrode. In some examples, the pacing mode controller 315 provides the NASPE/BPEG-defined DDD pacing mode in the normal operating mode.

In some examples, when in the second pacing mode, the pacing mode controller 315 paces at least one ventricle (V), without timing the pacing of the ventricle from an atrial cardiac event, when a V-V interval exceeds a specified ventricular interval (e.g., the NASPE/BPEG-defined VVI pacing mode). In some examples, when in the third pacing mode, the pacing mode controller 315 paces an atrium and, in response to the pace in the atrium, triggers pacing of at least one ventricle after expiration of a specified fixed or dynamic AV delay without regard to any intrinsic cardiac depolarization event occurring in the ventricle (e.g., the NASPE/BPEG-defined DOO pacing mode).

The pacing mode controller 315 includes a memory 320 integral to or communicatively coupled to the pacing mode controller 315. In some examples, the memory 320 includes a stress augmentation cycle memory area 325. The pacing mode controller 315 stores a statistic 330 related to the stress augmentation mode in the stress augmentation cycle memory area 325.

According to some examples, the statistic 330 is related to delivery of pacing in the stress augmentation mode. In some examples, the statistic 330 includes the total time pacing therapy is delivered according to the second and third pacing modes. In certain examples, the pacing mode controller 315 creates the statistic 330 by adding up the time the IMD 300 is in the second pacing mode during delivered intermittent pacing sessions (e.g., Pacing Mode A in FIG. 2), and adding up the time the IMD is in the third pacing mode during delivered intermittent pacing sessions (e.g., Pacing Mode B in FIG. 2).

In some examples, the statistic 330 includes the total number of electrical stimulation pulses delivered by the electrical stimulation circuit 310 during the stress augmentation mode. In some examples, the statistic 330 includes the total number of intrinsic V depolarizations sensed by the cardiac depolarization sensing circuit 305 during the stress augmentation mode. In some examples, the pacing mode controller 315 is configured (e.g., programmed) to provide a specified number of sessions of pacing in the stress augmentation mode (e.g., the intermittent pacing sessions in FIG. 2). The statistic 330 includes the total number of sessions of pacing in the stress augmentation mode that were completed. In certain examples, the statistic 330 includes the total number of sessions of pacing in the stress augmentation mode that remain to be delivered.

According to some examples, the statistic 330 is related to inhibiting the stress augmentation mode. In some examples, the statistic 330 includes the total number of times that the stress augmentation mode was not initiated as scheduled due to a high depolarization rate sensed by the cardiac depolarization sensing circuit 305. The pacing mode controller 315 may inhibit the stress augmentation because the depolarization rate exceeded a specified lowest tachyarrhythmia detection rate. The pacing mode controller 315 may inhibit the stress augmentation because the depolarization rate and/or a sensor included in the IMD 300 (e.g., an activity sensor or a respiration sensor) indicate the patient is exercising. In certain examples, the statistic 330 includes the total number of times that the stress augmentation mode was aborted due to the high depolarization rate.

In some examples, the statistic 330 includes the total number of times that the stress augmentation mode was aborted due to device reasons. In some examples, the IMD 300 includes a magnetic field sensor (e.g., a reed switch) communicatively coupled to the pacing mode controller 315. The device reasons may include aborting the stress augmentation mode when the IMD 300 detects a magnetic field, such as when a magnet is held near the IMD 300. In some examples, the MD 300 includes a communication circuit communicatively coupled to the pacing mode controller 315. The communication circuit is configured to communicate wirelessly with an external system. The device reasons may include aborting the stress augmentation mode when a command is received in the IMD 300 from the external system. The magnet and/or the external system give the patient or caregiver some external control in aborting or delaying a stress augmentation mode session.

Signal noise may sometimes interfere with the ability of the cardiac depolarization sensing circuit 305, or other sensing circuit of the IMD 300, to sense signals representative of physiologic events of the patient. For example, the IMD 300 may include multiple cardiac depolarization sensing circuits 305. Crosstalk between the circuits may prevent proper sensing of depolarization signals. Other sources of signal noise may prevent the IMD 300 from properly sensing other physiologic signals. In some examples, the IMD 300 includes a noise detection circuit communicatively coupled to the pacing mode controller 315. The device reasons for which the IMD 300 may abort stress augmentation mode include the IMD 300 detecting signal noise on a sensing circuit that exceeds a signal noise level threshold.

In some examples, the statistic 330 includes the total number of times that the stress augmentation mode was retried when the stress augmentation mode was not initiated as scheduled. In certain examples, the pacing mode controller 315 increments the statistic 330 whenever the stress augmentation mode was retried after the pacing mode controller 315 aborts, delays, or otherwise inhibits the stress augmentation mode.

In some examples, the statistic 330 includes the total number of times that a stress augmentation mode session was skipped by the pacing mode controller 315. The pacing mode controller 315 may be configured to deliver pacing therapy in recurrent stress augmentation mode sessions. The pacing mode controller 315 may skip a stress augmentation mode session when the currently scheduled stress augmentation session is delayed and runs into the next scheduled stress augmentation mode session. The pacing mode controller 315 may skip a stress augmentation mode session when a specified maximum retry count is reached.

According to some examples, the pacing mode controller 315 is configured to store a plurality of statistics related to the stress augmentation mode as a log in the stress augmentation cycle memory area 325, such as by creating log entries in the stress augmentation cycle memory area 325. In some examples, a log entry for a stress augmentation mode session includes a session start time. In certain examples, the log entry includes a start time of the second pacing mode and/or a start time of the third pacing mode. In some examples, the log entry includes a pacing rate at which the second pacing mode was delivered and/or a pacing rate at which the third pacing mode was delivered (the second and third pacing mode need not be delivered at the same pacing rate). In some examples, the log entry includes a NASPE/BPEG-defined pacing mode of the second pacing mode and/or a NASPE/BPEG-defined pacing mode of the third pacing mode. In some examples, the log entry includes a NASPE/BPEG-defined pacing mode used during the stress augmentation session together with a pacing rate at which the NASPE/BPEG-defined pacing mode was delivered.

In some examples, the log entry for a stress augmentation mode session includes a count of electrical stimulation pulses delivered during the second pacing mode and/or the third pacing mode during the session. In some examples, the log entry includes a count of intrinsic V depolarizations sensed during the second pacing mode and/or the third pacing mode. In some examples, the log entry includes a status of the stress augmentation mode session corresponding to the log entry. The status may include an indication whether the stress augmentation mode session was delivered, aborted, or suspended. In some examples, the log entry includes a number of retries attempted in the stress augmentation mode session.

In some examples, the log entry may include data related to a physiologic cardiovascular event of a subject recorded during the stress augmentation mode session. In certain examples, the cardiac depolarization sensing circuit 305 senses intracardiac electrograms. The IMD 300 may include a sampling circuit, coupled to the cardiac depolarization sensing circuit 305, to convert the sensed intracardiac signals into digitized samples. The log entry includes the samples of the electrogram sensed in a time relationship (e.g., during) the stress augmentation session. In some examples, the IMD 300 may include a different type of sensor in addition to, or instead of, the cardiac depolarization sensing circuit 305. The sensor provides an electrical sensor signal related to one or more physiologic cardiovascular events in the patient. Examples include, among other things, a heart sound sensor, a cardiac blood pressure sensor, a transthoracic impedance sensor, an intracardiac impedance sensor, a chemical sensor, an oxygen sensor, an accelerometer, and a temperature sensor. The log entry recorded data may include samples of the electrical sensor signal.

In certain examples, the log entry includes a measurement obtained from the data recorded during the stress augmentation mode session. The measurement may be taken from the sensed electrogram, such as an R-wave amplitude or width for example, or from another electrical sensor signal. In some examples, the IMD 300 includes a communication circuit and communicates a log entry to an external system.

Figure 4:
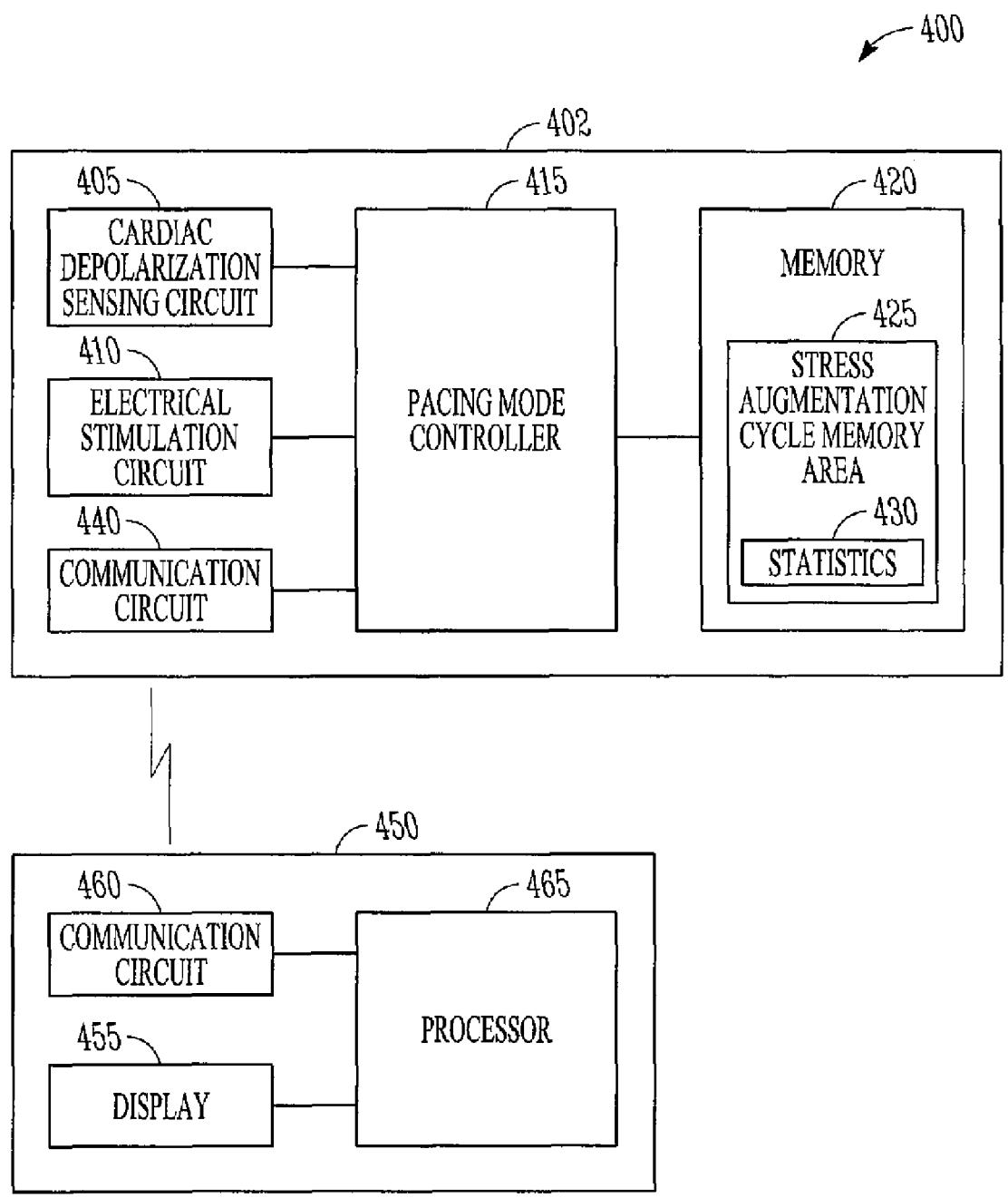
FIG. 4 is a block diagram of portions of an example of a system to provide intermittent pacing therapy in a stress augmentation mode.

FIG. 4 is a block diagram of portions of a system 400 to provide intermittent pacing therapy in a stress augmentation mode. The system 400 includes an implantable device, such as an IMD 402, and an external device 450. The IMD 402 includes at least one implantable cardiac depolarization sensing circuit 405, an electrical stimulation circuit 410, and a pacing mode controller 415. The pacing mode controller 415 delivers pacing therapy according to a first mode that is a normal operating mode. The pacing mode controller 415 also delivers intermittent pacing therapy in a stress augmentation mode.

When switched from the normal operating mode to the stress augmentation mode, the pacing mode controller 415 delivers pacing therapy according to a second pacing mode and a third pacing mode which increase mechanical stress on at least a particular portion of the ventricle as compared to the pacing therapy delivered during the first pacing mode. The pacing mode controller 415 alternates pacing therapy between the second and third pacing modes when switched from the normal operating mode to a stress augmentation mode.

The IMD 402 includes a memory 420 having stress augmentation cycle memory area 425 to store a plurality of statistics 430 related to the stress augmentation mode. The IMD 402 also includes a communication circuit 440 to communicate wirelessly with a second device. The second device may be the external device 450 or a second IMD. The IMD 402 communicates a plurality of stored statistics related to the stress augmentation mode to the second device via the communication circuit 440.

The external device 450 may be an IMD programmer. The external device 450 includes a programming interface display 455, a communication circuit 460 configured to communicate information with the implantable device, and a processor 465. The processor 465 receives the statistics 430 related to the stress augmentation mode from the IMD 402 and presents the statistics 430 in a multilevel display. In some examples, a multilevel display is configured to display information by organizing the information into different display screens for the different multiple levels. In certain examples, the display screens are organized hierarchically.

In some examples, the IMD 402 communicates, to the external device 450, a statistic related to stress augmentation mode and at least one log entry. The log entry corresponds to a stress augmentation mode session. The processor 465 of the external device 450 presents on the display 455 a first display level that includes the statistic related to delivery of pacing in the stress augmentation mode, and presents a second display level that includes the log entry for the stress augmentation mode session.

In some examples, the IMD 402 communicates, to the external device 450, a statistic related to delivery of pacing in the stress augmentation mode and data related to a physiologic cardiovascular event of a subject recorded by the implantable device during a stress augmentation mode session. The processor 465 presents on the display 455 a first display level that includes the statistic related to delivery of pacing in the stress augmentation mode, and presents a second display level that includes the recorded data related to a physiologic cardiovascular event of the subject.

In some examples, the IMD 402 communicates, to the external device 450, a statistic related to delivery of pacing in the stress augmentation mode and a statistic related to inhibiting the stress augmentation mode. The processor 465 presents on the display 455 a first display level that includes the statistic related to delivery of pacing in the stress augmentation mode, and a second display level that includes the statistic related to inhibiting the stress augmentation mode. In some examples, the IMD 402 additionally communicates at least one log entry for a stress augmentation mode session, and communicates data related to a physiologic cardiovascular event of a patient or subject recorded by the IMD 402 during the stress augmentation mode session. The processor 465 presents a third display level that includes the log entry for the stress augmentation session, and presents a fourth display level that includes the recorded data related to a physiologic cardiovascular events of the subject.

In certain examples, the external device 450 communicates with the IMD 402 via a third device, such as a repeater that rebroadcasts information it receives. The IMD 402 communicates the statistics 430 related to the stress augmentation mode to the external device 450 via the third device.

Figure 5:
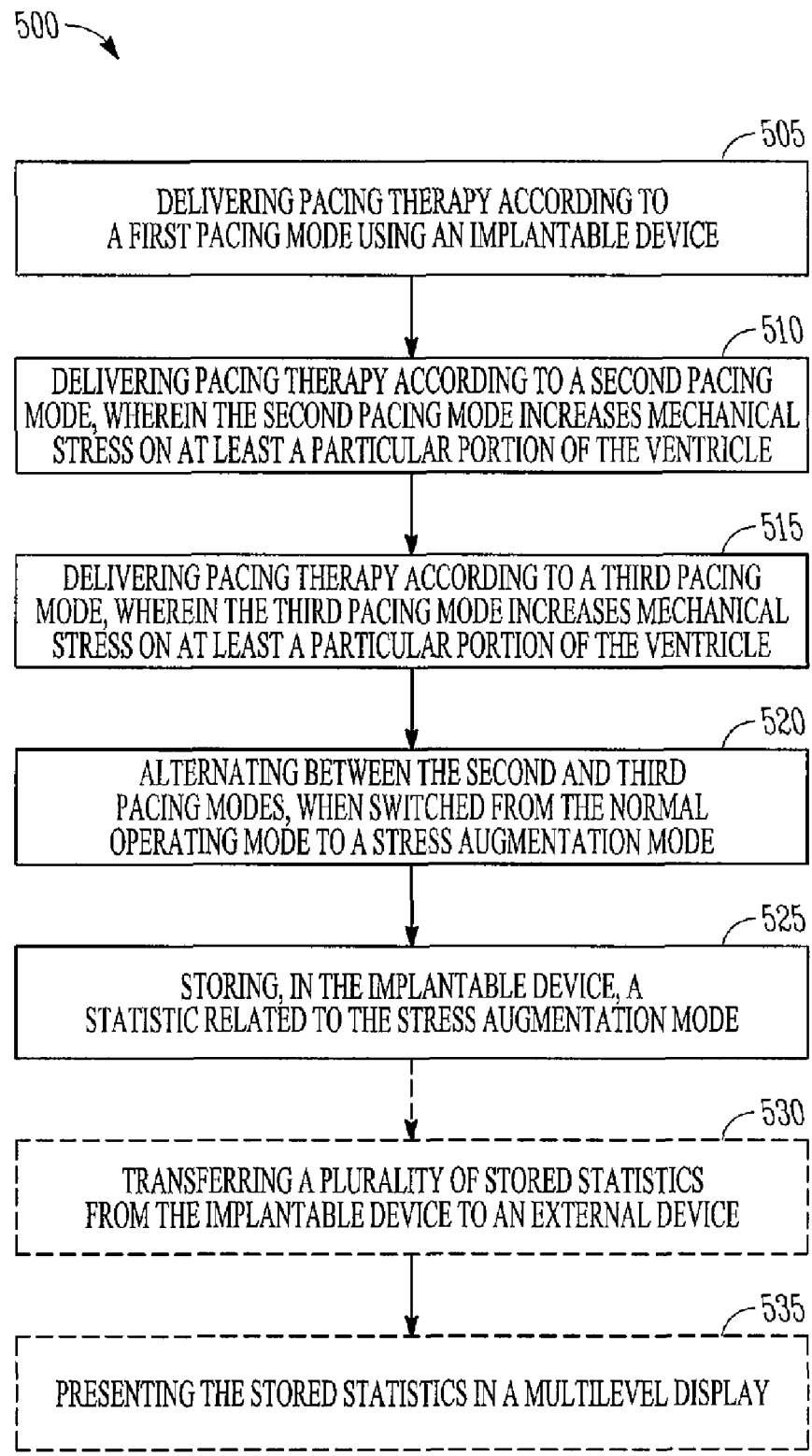
FIG. 5 is a flow diagram of an example of a method of providing intermittent pacing therapy in a stress augmentation mode.

FIG. 5 is a flow diagram of an example of a method 500 of providing intermittent pacing therapy in a stress augmentation mode. At block 505, pacing therapy is delivered according to a first pacing mode using an implantable device. The first pacing is a normal operating mode that allows for regular depolarizations to occur in the heart chamber (e.g., the NASPE/BPEG-defined DDD pacing mode).

At block 510, pacing therapy is delivered by the according to a second pacing mode using the implantable device. The second pacing mode increases mechanical stress on at least a particular portion of the ventricle as compared to the pacing therapy delivered during the first pacing mode. At block 515, pacing therapy is delivered according to a third pacing mode by the implantable device. The third pacing mode also increases mechanical stress on at least a particular portion of the ventricle as compared to the pacing therapy delivered during the first pacing mode.

At block 520, when the implantable device is switched from the normal operating mode to a stress augmentation mode, the pacing therapy alternates between the second and third pacing modes. The intermittent pacing that alternates between the second and third pacing modes is designed to increase ventricular dyssynchrony to cause stress in regional areas of the myocardial wall. Providing this intermittent regional stress stops the deterioration of hemodynamic performance of a HF patient, such as by stopping the progression of ventricular dilatation for example.

At block 525, a statistic related to the stress augmentation mode is stored in the implantable device. In some examples, the stored statistic is related to delivery of pacing in the stress augmentation mode. In some examples, the stored statistic is related to inhibiting the stress augmentation mode.

According to some examples, a plurality of statistics related to the stress augmentation mode is stored as a log entry in the implantable device. In some examples, at block 530, a plurality of stored statistics from the implantable device is transferred to an external device. At block 535, the statistics are presented in a multilevel display on the external device.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    at least one implantable cardiac depolarization sensing circuit configured to obtain a sensed depolarization signal from a ventricle;
    an electrical stimulation circuit, configured to provide pacing electrical stimulation energy to at least one implantable electrode in the ventricle;
    a memory; and
    a pacing mode controller communicatively coupled to the cardiac depolarization sensing circuit, the electrical stimulation circuit, and the memory, the pacing mode controller configured to:
        deliver pacing therapy according to a first mode, wherein the first mode is a normal operating mode;
        deliver pacing therapy according to a second pacing mode, wherein the second pacing mode increases mechanical stress on at least a particular portion of the ventricle as compared to the pacing therapy delivered during the first pacing mode;
        deliver pacing therapy according to a third pacing mode different from the second pacing mode, wherein the third pacing mode increases mechanical stress on at least a particular portion of the ventricle as compared to the pacing therapy delivered during the first pacing mode; and
        alternate between the second and third pacing modes when switched from the normal operating mode to a stress augmentation mode;
    wherein the memory includes a stress augmentation cycle memory area; and
    wherein the pacing mode controller is configured to store information related to the stress augmentation mode in the stress augmentation cycle memory area.

2. The apparatus of claim 1, wherein the information related to the stress augmentation mode is a statistic related to delivery of pacing in the stress augmentation mode and includes at least one of:
    a total time pacing therapy is delivered according to the second and third pacing modes;
    a total number of electrical stimulation pulses delivered during the stress augmentation mode;
    a total number of sensed intrinsic ventricular depolarizations during the stress augmentation mode;
    a total number of sessions of pacing in the stress augmentation mode that were completed; or
    a total number of sessions of pacing in the stress augmentation mode that remain to be delivered.

3. The apparatus of claim 1, wherein the information related to the stress augmentation mode is a statistic related to inhibiting the stress augmentation mode and includes at least one of:
    a total number of times that the stress augmentation mode was not initiated as scheduled due to high depolarization rate of at least one of an atrium or ventricle;
    a total number of times that the stress augmentation mode was aborted due to high depolarization rate;
    a total number of times that the stress augmentation mode was aborted due to device reasons;
    a total number of times that the stress augmentation mode was retried when the stress augmentation mode was not initiated as scheduled; or
    a total number of times that a stress augmentation mode session was skipped.

4. The apparatus of claim 1, wherein the pacing mode controller is configured to store a plurality of statistics related to the stress augmentation mode as a log in the stress augmentation cycle memory area.

5. The apparatus of claim 4, wherein the pacing mode controller is configured to create, in the stress augmentation cycle memory area, a log entry for a stress augmentation mode session that includes at least one of:
    a session start time;
    a start time of the second pacing mode;
    a start time of the third pacing mode;
    a pacing rate at which the second pacing mode was delivered;
    a NASPE/BPEG-defined pacing mode of the second pacing mode;
    a pacing rate at which the third pacing mode was delivered;
    a NASPE/BPEG-defined pacing mode of the third pacing mode;
    a count of electrical stimulation pulses delivered during the second pacing mode;

a count of V intrinsic depolarizations sensed during the third pacing mode;
a status of the stress augmentation mode session;
a number of retries attempted in the stress augmentation mode session;
data related to a physiologic cardiovascular event of a subject recorded during the stress augmentation mode session; or
a measurement obtained from the recorded data.

6. The apparatus of claim 4, wherein the pacing mode controller is configured to create, in the stress augmentation cycle memory area, a log entry for a stress augmentation mode session that includes a NASPE/BPEG-defined pacing mode used during the stress augmentation session together with a pacing rate at which the NASPE/BPEG-defined pacing mode was delivered.

7. A system comprising:
an implantable device including:
at least one implantable cardiac depolarization sensing circuit configured to obtain a sensed depolarization signal from a ventricle;
an electrical stimulation circuit, configured to provide pacing electrical stimulation energy to at least one implantable electrode in the ventricle;
a first communication circuit; and
a pacing mode controller communicatively coupled to the cardiac depolarization sensing circuit, the electrical stimulation circuit, and the communication circuit, the pacing mode controller configured to:
deliver pacing therapy according to a first mode, wherein the first mode is a normal operating mode;
deliver pacing therapy according to a second pacing mode, wherein the second pacing mode increases mechanical stress on at least a particular portion of the ventricle as compared to the pacing therapy delivered during the first pacing mode;
deliver pacing therapy according to a third pacing mode different from the second pacing mode, wherein the third pacing mode increases mechanical stress on at least a particular portion of the ventricle as compared to the pacing therapy delivered during the first pacing mode;
alternate between the second and third pacing modes, when switched from the normal operating mode to a stress augmentation mode; and
communicate a plurality of stored statistics related to the stress augmentation mode to a second device via the first communication circuit; and
an external device including:
a display;
a second communication circuit configured to communicate information with the implantable device; and
a processor, communicatively coupled to the display and the second communication circuit, wherein the processor is configured to:
receive the statistics from the implantable device; and
present the statistics in a multilevel display.

8. The system of claim 7, wherein the implantable device is configured to communicate, to the external device, a statistic related to delivery of pacing in the stress augmentation mode and at least one log entry for a stress augmentation mode session, and
wherein the processor of the external device is configured to:
present a first display level that includes the statistic related to delivery of pacing in the stress augmentation mode; and
present a second display level that includes the log entry for a stress augmentation mode session.

9. The system of claim 7, wherein the implantable device is configured to communicate, to the external device, statistic related to delivery of pacing in the stress augmentation mode and data related to a physiologic cardiovascular events of a subject recorded by the implantable device during a stress augmentation mode session, and
wherein the processor of the external device is configured to:
present a first display level that includes the statistic related to delivery of pacing in the stress augmentation mode; and
present a second display level that includes the recorded data related to a physiologic cardiovascular event of the subject.

10. The system of claim 7, wherein the implantable device is configured to communicate, to the external device, a statistic related to delivery of pacing in the stress augmentation mode and a statistic related to inhibiting the stress augmentation mode, and
wherein the processor of the external device is configured to:
present a first display level that includes the statistic related to delivery of pacing in the stress augmentation mode; and
present a second display level that includes the statistic related to inhibiting the stress augmentation mode.

11. The system of claim 10, wherein the implantable device is configured to communicate, to the external device, at least one log entry for stress augmentation mode session and to communicate data related to a physiologic cardiovascular events of a subject recorded by the implantable device during the stress augmentation mode session, and
wherein the processor of the external device is configured to:
present a third display level that includes the log entry for the stress augmentation session; and
present a fourth display level that includes the recorded data related to a physiologic cardiovascular event of the subject.

12. The system of claim 7, including a third device configured to communicate with the implantable device and the external device, and wherein the implantable device communicates the statistics related to the stress augmentation mode to the external device via the third device.

13. A method comprising:
sensing a depolarization signal from a ventricle;
delivering pacing therapy according to a first pacing mode using an implantable device, wherein the first pacing mode is a normal operating mode;
delivering pacing therapy according to a second pacing mode, wherein the second pacing mode increases mechanical stress on at least a particular portion of the ventricle as compared to the pacing therapy delivered during the first pacing mode;
delivering pacing therapy according to a third pacing mode different from the second pacing mode, wherein the third pacing mode increases mechanical stress on at least a particular portion of the ventricle as compared to the pacing therapy delivered during the first pacing mode;
alternating between the second and third pacing modes, when switched from the normal operating mode to a stress augmentation mode; and
storing, in the implantable device, information related to the stress augmentation mode.

14. The method of claim 13, wherein storing information related to the stress augmentation mode includes storing a statistic related to delivery of pacing in the stress augmentation mode, including at least one of:
- a total time pacing therapy is delivered according to the second and third pacing modes;
- a total number of ventricular (V) pace stimulation pulses delivered during the stress augmentation mode;
- a total number of sensed intrinsic V depolarizations during the stress augmentation mode;
- a total number of sessions of pacing in the stress augmentation mode that were completed; or
- a total number of sessions of pacing in the stress augmentation mode that remains to be delivered.

15. The method of claim 13, wherein storing information related to the stress augmentation mode includes storing a statistic related to inhibiting the stress augmentation mode, including at least one of:
- a total number of times that the stress augmentation mode was not initiated as scheduled due to high depolarization rate of at least one of an atrium or ventricle;
- a total number of times that the stress augmentation mode was aborted due to high depolarization rate;
- a total number of times that the stress augmentation mode was aborted due to device reasons;
- a total number of times that the stress augmentation mode was retried when the stress augmentation mode was not initiated as scheduled; or
- a total number of times that a stress augmentation mode session was skipped.

16. The method of claim 13, wherein storing information related to the stress augmentation mode includes storing a plurality of statistics as a log in a memory of the implantable device.

17. The method of claim 16, wherein storing statistics as a log includes creating a log entry in the implantable device for a stress augmentation session that includes at least one of:
- a session start time;
- a start time of the second pacing mode;
- a start time of the third pacing mode;
- a pacing rate at which the second pacing mode was delivered;
- a NASPE/BPEG-defined pacing mode of the second pacing mode;
- a pacing rate at which the third pacing mode was delivered;
- a NASPE/BPEG-defined pacing mode of the third pacing mode;
- a count of electrical stimulation pulses delivered during the second pacing mode;
- a count of V intrinsic depolarizations sensed during the third pacing mode;
- a status of the stress augmentation mode session;
- a number of retries attempted in the stress augmentation mode session;
- data related to a physiologic cardiovascular event of a subject recorded during the stress augmentation mode session; or
- a measurement obtained from the recorded data.

18. The method of claim 13, including:
transferring a plurality of stored statistics from the implantable device to an external device; and
presenting the stored statistics in a multilevel display.

19. The method of claim 18, wherein presenting the stored statistics in a multilevel display includes:
presenting a first display level that includes a statistic related to delivery of pacing in the stress augmentation mode; and
presenting a second display level that includes a statistic related to inhibiting the stress augmentation mode.

20. The method of claim 18, wherein presenting the stored statistics in a multilevel display includes:
presenting a first display level that includes a statistic related to delivery of pacing in the stress augmentation mode; and
presenting a second display level that includes at least one stress augmentation session log entry stored in the implantable device.

21. The method of claim 18, wherein presenting the stored statistics in a multilevel display includes:
presenting a first display level that includes a statistic related to delivery of pacing in the stress augmentation mode; and
presenting a second display level that includes data related to a physiologic cardiovascular event of a subject recorded by the implantable device during a stress augmentation mode session.

* * * * *